(12) United States Patent
Okazaki

(10) Patent No.: US 9,649,017 B2
(45) Date of Patent: May 16, 2017

(54) ENDOSCOPE

(71) Applicant: OLYMPUS CORPORATION, Tokyo (JP)

(72) Inventor: Tsugio Okazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 14/507,134

(22) Filed: Oct. 6, 2014

(65) Prior Publication Data

US 2015/0087910 A1 Mar. 26, 2015

Related U.S. Application Data

(63) Continuation of application No. PCT/JP2014/060626, filed on Apr. 14, 2014.

(30) Foreign Application Priority Data

May 29, 2013 (JP) ................ 2013-113227

(51) Int. Cl.
*A61B 1/00* (2006.01)
*A61B 1/005* (2006.01)
*G02B 23/24* (2006.01)
*A61B 1/04* (2006.01)

(52) U.S. Cl.
CPC .......... *A61B 1/0055* (2013.01); *A61B 1/0052* (2013.01); *A61B 1/0057* (2013.01); *G02B 23/2476* (2013.01)

(58) Field of Classification Search
CPC .................................... G02B 23/2476
See application file for complete search history.

(56) References Cited

U.S. PATENT DOCUMENTS 5,271,382 A 12/1993 Chikama
2013/0096384 A1 4/2013 Arai

FOREIGN PATENT DOCUMENTS

| EP | 0524755 A1 | 1/1993 |
|----|---|---|
| EP | 2578139 A1 | 4/2013 |
| JP | S61-188701 U | 11/1986 |
| JP | S62-79033 A | 4/1987 |
| JP | 02-074231 A | 3/1990 |
| JP | H3-98802 U | 10/1991 |
| JP | H4-61501 U | 5/1992 |
| JP | 05-023291 A | 2/1993 |
| JP | 07-116104 A | 5/1995 |
| JP | 2012040308 A | 3/2012 |
| JP | 5153970 B2 | 2/2013 |
| WO | WO 2012/120955 A1 | 9/2012 |

*Primary Examiner* — Timothy J Neal
(74) *Attorney, Agent, or Firm* — Scully, Scott, Murphy & Presser, P.C.

(57) ABSTRACT

An endoscope includes an insertion portion, a first bending portion, a second bending portion, a bending operation wire, a first coil sheath, a switching mechanism, a guide, a first region of the guide, a second region of the guide, and a central part formed between the first region and the second region on an inner surface of the guide, protruding inside more than the first region and the second region and formed to be longer than a coil elemental wire making up the first coil sheath.

8 Claims, 13 Drawing Sheets

ENDOSCOPE

CROSS REFERENCE TO RELATED APPLICATION

This application is a continuation application of PCT/JP2014/060626 filed on Apr. 14, 2014 and claims benefit of Japanese Application No. 2013-113227 filed in Japan on May 29, 2013, the entire contents of which are incorporated herein by this reference.

BACKGROUND OF THE INVENTION

1. Field of the Invention

The present invention relates to an endoscope provided with a first bending portion bendable in a plurality of directions and a second bending portion bendable in a plurality of directions in an insertion portion inserted into a subject to be examined.

2. Description of the Related Art

In recent years, endoscopes inserted into subjects to be examined have been widely used in medical and industrial fields. By inserting its elongated insertion portion into the subject, an endoscope can be used to observe a region to be examined of the subject and perform treatment or the like.

Here, a configuration is well known which is provided with, for example, a bending portion which is bendable in a plurality of directions at an insertion portion of an endoscope. The bending portion improves a progressive property of the insertion portion of a crooked part inside a duct. The bending portion also makes variable the observation direction of an observation optical system provided at a distal end portion located ahead (hereinafter simply referred to as "forward") of the bending portion in a longitudinal direction in the insertion portion.

Since a plurality of bending pieces are connected together along the longitudinal direction of the insertion portion, the bending portion is normally configured to be freely bendable in four directions: up, down, left and right. More specifically, the bending portion can be freely bent in any one of the four directions: up, down, left and right, by pulling any one of the four bending operation wires (hereinafter, simply referred to as "wires") from an operation section.

Note that the four wires are inserted into the insertion portion so as to be freely movable forward or backward in the longitudinal direction and a distal end of the wire in the longitudinal direction (hereinafter, simply referred to as "distal end") is fixed to a bending piece located closest to the distal end side in the longitudinal direction (hereinafter, simply referred to as "distal end side") among the plurality of bending pieces.

Note that the bending portion formed to have a shorter length in the longitudinal direction, that is, the bending portion with the smaller bending radius can turn in a small turning circle. This improves ease of passage of the distal end portion of the insertion portion with respect to the crooked part in the duct, causes the observation optical system provided at the distal end portion to easily approach the region to be examined, and is therefore advantageous.

This is because when the bending portion is formed so as to be long in the longitudinal direction, if a medical endoscope, for example, is inserted into the large intestine, the distal end portion strikes the crooked part of the large intestine, causing the field of view to be easily lost. That is, the shorter the bending portion, the less likely it is for the distal end portion to strike the intestinal wall at the crooked part. Note that, to reduce the length of the bending portion, it is only necessary to reduce the number of bending pieces connected.

However, when the bending portion is formed to be short, if the bending portion is bent, its distal end portion is caused to pass through the crooked part of the large intestine, the insertion portion is pushed in from a proximal end side in the longitudinal direction (hereinafter simply referred to as "proximal end side") to make an attempt to move the distal end portion ahead of the crooked part, that is, to cause the bending part to pass through the crooked part, this results in the bending portion thrusting the intestinal wall—a so-called stick phenomenon. This makes it difficult for the bending portion to pass through, and as a consequence insertability of the insertion portion may deteriorate.

Furthermore, in the case of a medical endoscope, the following technique is generally used. After the distal end portion passes through the crooked part, the crooked part is straightened by pulling the proximal end side of the insertion portion with the distal end portion and the bending portion caught in a tissue in the body cavity first. Then, the insertion portion is pushed in from the proximal end side to allow the bending portion to pass through the crooked part.

FIG. 13 is a diagram schematically illustrating a state in which a second bending portion together with a first bending portion is bent rightward (RIGHT direction) on a distal end side of an insertion portion of a conventional endoscope and FIG. 14 is a cross-sectional view along a line XIV-XIV in FIG. 13 of a first bending portion and a second bending portion.

Japanese Patent Application Laid-Open Publication No. 7-116104 discloses a configuration as shown in FIG. 13 in which two bending portions 110 are provided as a first bending portion 101 and a second bending portion 102 on a distal end side of an insertion portion 106. Furthermore, Japanese Patent Application Laid-Open Publication No. 7-116104 discloses a configuration in which the first bending portion 101 is singly bendable and the second bending portion 102 is bendable together with the first bending portion 101, and it is thereby possible to keep constant the length of the bending portion 110 in a longitudinal direction S. In addition, Japanese Patent Application Laid-Open Publication No. 7-116104 also discloses a configuration in which only the first bending portion 101 is freely bendable, and it is thereby possible to reduce the bending radius.

More specifically, as shown in FIG. 13 and FIG. 14, Japanese Patent Application Laid-Open Publication No. 7-116104 discloses a configuration in which perimeters of four wires $111r$, $111l$, $111u$ and $111d$ (wires $111u$ and $111d$ are not shown) inserted in the insertion portion 106 are respectively covered with first coil sheaths (hereinafter referred to as "inside coil sheaths") $112r$, $112l$, $112u$ and $112d$ (inside coil sheaths $112u$ and $112d$ are not shown).

Japanese Patent Application Laid-Open Publication No. 7-116104 also discloses a configuration in which a distal end of each inside coil sheath $112r$ to $112d$ is fixed to a connection pipe sleeve 115 that connects a first bending piece $101k$ located at a rearmost position (hereinafter simply referred to as "rear") in the longitudinal direction S among a plurality of first bending pieces $101k$ making up the first bending portion 101 and a second bending piece $102k$ located at a frontmost position in the longitudinal direction S among a plurality of second bending pieces $102k$ making up the second bending portion 102. A configuration is further disclosed in which a proximal end of each inside coil sheath $112r$ to $112d$ is simultaneously switched between a fixed state and an unfixed state by a switching mechanism provided in the operation section.

Japanese Patent Application Laid-Open Publication No. 7-116104 further discloses a configuration in which perimeters of the respective inside coil sheaths $112r$ to $112d$ are covered with second coil sheaths (hereinafter simply referred to as "outside coil sheaths") $113r$, $113l$, $113u$ and $113d$ (outside coil sheaths $113u$ and $113d$ are not shown). Japanese Patent Application Laid-Open Publication No. 7-116104 also discloses a configuration in which a distal end of each outside coil sheath $113r$ to $113d$ is fixed to a distal end of a flexible tubular part $105$ and a proximal end of each outside coil sheath $113r$ to $113d$ is fixed to a proximal end side of the flexible tubular part.

On the other hand, while the fixing of the proximal end of each inside coil sheath $112r$ to $112d$ is canceled if, for example, the wire $111r$ is pulled using the bending operation mechanism provided in the operation section, the first bending portion $101$ and the second bending portion $102$ are bent toward the RIGHT side with the distal end of the outside coil sheath $113r$ as a starting point. On the other hand, while the proximal end of each inside coil sheath $112r$ to $112d$ is simultaneously fixed if, for example, the wire $111r$ is pulled, only the first bending portion $101$ is bent toward the RIGHT side with the distal end of the inside coil sheath $112r$ as a starting point.

FIG. 15 is a cross-sectional view along a line XV-XV in FIG. 14 illustrating an example where inside the second bending piece making up the second bending portion, a left inside coil pipe that moves toward the RIGHT side in FIG. 14 is shifted toward the DOWN side and FIG. 16 is a cross-sectional view illustrating an example where the left inside coil pipe that moves toward the RIGHT side in FIG. 14 is shifted toward the UP side.

FIG. 17 is a partial cross-sectional view along a line XVII-XVII in FIG. 13 illustrating an example where the second bending portion is bent deviated from the RIGHT side to the DOWN side and FIG. 18 is a partial cross-sectional view illustrating an example where the second bending portion in FIG. 13 is bent deviated from the RIGHT side to the UP side.

Note that in FIG. 15 and FIG. 16, each wire $111r$ to $111d$ is omitted for simplicity of illustration.

Here, as shown in FIG. 15 and FIG. 16, various components are provided in the second bending piece $102k$ such as a signal cable $120$ that extends from an image pickup unit provided in the distal end portion $103$ of the insertion portion $106$, a treatment instrument insertion duct $121$ that is opened in a front end face $103s$, a forward water feeding channel $122$ and a light guide $123$ that supplies illuminating light to the front end face $103s$ of the distal end portion $103$. Since the positions of the various components in the second bending piece $102k$ are not fixed, the positions are always not constant.

Thus, the left inside coil sheath $112l$ that moves toward the RIGHT side as the second bending portion $102$ is bent toward the RIGHT side comes into contact with each component in the second bending piece $102k$ as it moves. Accordingly, the left inside coil sheath $112l$ does not always move from the UP-DOWN direction toward the exactly 90° RIGHT side, but it may be shifted from the RIGHT side toward the DOWN side while moving toward the RIGHT side as shown in FIG. 15. In addition, the left inside coil sheath $112l$ may be shifted from the RIGHT side toward the UP side while moving toward the RIGHT side as shown in FIG. 16.

Note that in this case, the up inside coil sheath $112u$ and the down inside coil sheath $112d$ also slightly move toward the RIGHT side as shown in FIG. 15 and FIG. 16.

Thus, as shown in FIG. 15, if the left inside coil sheath $112l$ is shifted from the RIGHT side toward the DOWN side while moving toward the RIGHT side, the bending direction of the second bending portion $102$ is also shifted from the RIGHT side toward the DOWN side as shown in FIG. 17. As a result, if the left inside coil sheath $112l$ is shifted from the RIGHT side toward the UP while moving toward the RIGHT side as shown in FIG. 16, the bending direction of the second bending portion $102$ is also shifted from the RIGHT side toward the UP side as shown in FIG. 18.

FIG. 19 is an enlarged cross-sectional view of a wire guide section provided for the first bending piece shown in FIG. 14 and FIG. 20 is an enlarged cross-sectional view of the left inside coil pipe in FIG. 14.

Here, as shown in FIG. 14, a configuration is well known in which each wire $111r$ to $111d$ is inserted into the first bending piece $101k$ and a plurality of guides $130$ which are tubular guide sections that hold each wire $111r$ to $111d$ to run along the inner surface of the first bending piece $101k$.

Thus, when the plurality of guides $130$ shown in FIG. 14 are fixed to the second bending pieces $102k$, each inside coil sheath $112r$ to $112d$ is inserted into each guide $130$, and the guide $130$ holds each inside coil sheath $112r$ to $112d$ to run along the inner surface of the second bending piece $102k$, if the second bending portion $102$ is bent, for example, toward the RIGHT side, it is supposed to be able to prevent each inside coil sheath $112l$, $112u$, $112d$ from moving toward the RIGHT side inside the second bending piece $102k$.

However, with a plurality of stranded wires being twisted, the wire $111r$ to $111d$ are configured to be rigid. For this reason, the wires $111r$ to $111d$ are never disordered in shape even when they come into contact with the inner surfaces $130n$ of the guides $130$ and less likely to wear out. However, the inside coil sheaths $112r$ to $112d$ are configured to be flexible so as to be bendable together with the second bending portion $102$ by winding an elemental wire $112s$ as shown in FIG. 20. Accordingly, when the left inside coil sheath $112l$ slides forward or backward in the longitudinal direction S through a through hole $130i$ of the guide $130$ as the second bending portion $102$ is bent toward the RIGHT direction, if the inside coil sheaths $112r$ to $112d$ come into contact with an inner surface $130n$ or a corner section $130c$ of a distal end $130s$ or a proximal end $130k$ as shown in FIG. 19, an array of the elemental wire $112s$ is disordered as shown in FIG. 20, and a so-called pitch shift a occurs.

SUMMARY OF THE INVENTION

An endoscope according to one aspect of the present invention includes an insertion portion that is inserted into a subject, a bendable first bending portion that is provided on a distal end side of the insertion portion, a bendable second bending portion that is provided in the insertion portion closer to a proximal end side than the first bending portion, a bending operation wire that is inserted into the insertion portion, a distal end of the bending operation wire being fixed to the first bending portion, a first coil sheath that is inserted into the second bending portion, the bending operation wire being inserted thereinto so as to be freely movable in a longitudinal direction of the insertion portion and a distal end of the first coil sheath being fixed to a distal end side of the second bending portion, a switching mechanism that switches between fixing and unfixing of a proximal end of the first coil sheath and moves the proximal end of the first coil sheath in the longitudinal direction inside the insertion portion when the proximal end of the first coil sheath is unfixed, a guide section that is fixed to an inner surface of the second bending portion, including a through hole that the first coil sheath penetrates in the longitudinal direction, and holding the first coil sheath penetrating the through hole so that the first coil sheath runs along the inner surface of the second bending portion, a first region that is formed into a curved surface on an inner surface on a distal end side of the guide section, a second region that is formed into a curved surface on an inner surface on a proximal end side of the guide section, and a central part that is formed between the first region and the second region on the inner surface of the guide section, has a shape protruding more inside in a diameter direction of the guide section than the first region and the second region and is formed to be longer than a length in the longitudinal direction of a coil elemental wire making up the first coil sheath.

DETAILED DESCRIPTION OF THE PREFERRED EMBODIMENTS

Hereinafter, embodiments of the present invention will be described with reference to the accompanying drawings.

First Embodiment

Figure 1:
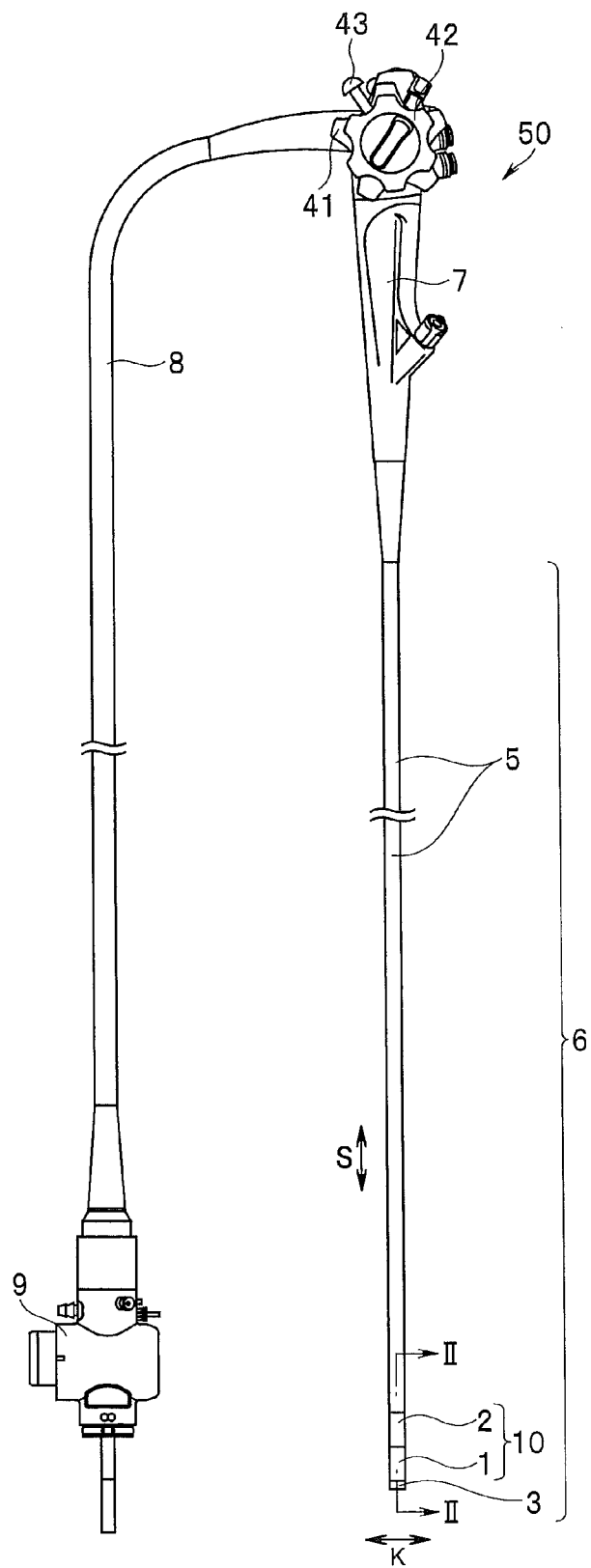
FIG. 1 is a diagram illustrating an appearance of an endoscope of a first embodiment.

FIG. 1 is a diagram illustrating an appearance of an endoscope of a first embodiment.

As shown in FIG. 1, an endoscope 50 is provided with an insertion portion 6 inserted into a subject and an operation section 7 connected to a proximal end of the insertion portion 6. The endoscope 50 is also provided with a universal cord 8 that extends from the operation section 7 and a connector 9 provided at an extending end of the universal cord 8. Note that the endoscope 50 is electrically connected to outside apparatuses such as a control apparatus and an illumination apparatus via the connector 9.

Main parts of the insertion portion 6 are configured by including an elongated flexible tubular part 5 that extends along a longitudinal direction S of the insertion portion 6, a bending portion 10 located ahead of the flexible tubular part 5 and a distal end portion 3 located ahead of the bending portion 10.

An image pickup unit, which is not shown, for picking up an image of an inside of a subject and an illumination unit, which is not shown, for supplying illuminating light into the inside of the subject are provided inside the distal end portion 3.

The bending portion 10 is constructed of a first bending portion 1 and a second bending portion 2 located between the first bending portion 1 and the flexible tubular part 5 in the longitudinal direction S.

The first bending portion 1 is singly freely bendable in, for example, four directions of up, down, left and right by bending operation knobs 41 and 42 provided in the operation section 7 which will be described later.

The second bending portion 2 is freely bendable together with the first bending portion 1 in, for example, four directions of up, down, left and right by the bending operation knobs 41 and 42 provided in the operation section 7 which will be described later. Note that the configurations of the first bending portion 1 and the second bending portion 2 will be described later.

The operation section 7 is provided with the bending operation knob 41 that makes up a bending operation mechanism that causes the first bending portion 1 or the first bending portion 1 and the second bending portion 2 to bend in the up-down direction.

The operation section 7 is also provided with the bending operation knob 42 that makes up a bending operation mechanism that causes the first bending portion 1 or the first bending portion 1 and the second bending portion 2 to bend in the right-left direction.

An up-down bending pulley, which is not shown, making up a bending operation mechanism that causes the first bending portion 1 or the first bending portion 1 and the second bending portion 2 to bend in the up-down direction by pulling/loosening bending operation wires 11$u$ and 11$d$ (see FIG. 4) inserted into the insertion portion 6 and the operation section 7, which will be described later, by rotating together with the bending operation knob 41 is provided in the operation section 7.

Furthermore, a right-left bending pulley, which is not shown, making up a bending operation mechanism that causes the first bending portion 1 or the first bending portion 1 and the second bending portion 2 to bend in the right-left direction by pulling/loosening bending operation wires 11$r$ and 11$l$ (see FIG. 4), which will be described later, inserted into the insertion portion 6 and the operation section 7 by rotating together with the bending operation knob 42 is provided in the operation section 7.

Note that since the configurations of the up-down bending pulley and the right-left bending pulley are well known, detailed description thereof using drawings will be omitted.

A switching lever 43 is provided in the operation section 7 which makes up a switching mechanism for switching between fixing and unfixing of the proximal ends of first coil sheaths 12$r$, 12$l$, 12$u$ and 12$d$ inserted into the insertion portion 6 and the operation section 7 which will be described later.

A switching member is also provided in the operation section 7 which makes up a switching mechanism for switching between fixing and unfixing of the proximal ends of the first coil sheaths 12$u$, 12$d$, 12$r$ and 12$l$ according to operation of the switching lever 43. Note that since the configuration of the switching member is well known, detailed description thereof using drawings will be omitted.

Next, configurations of the first bending portion 1 and the second bending portion 2 will be described using FIG. 2 to FIG. 5.

Figure 2:
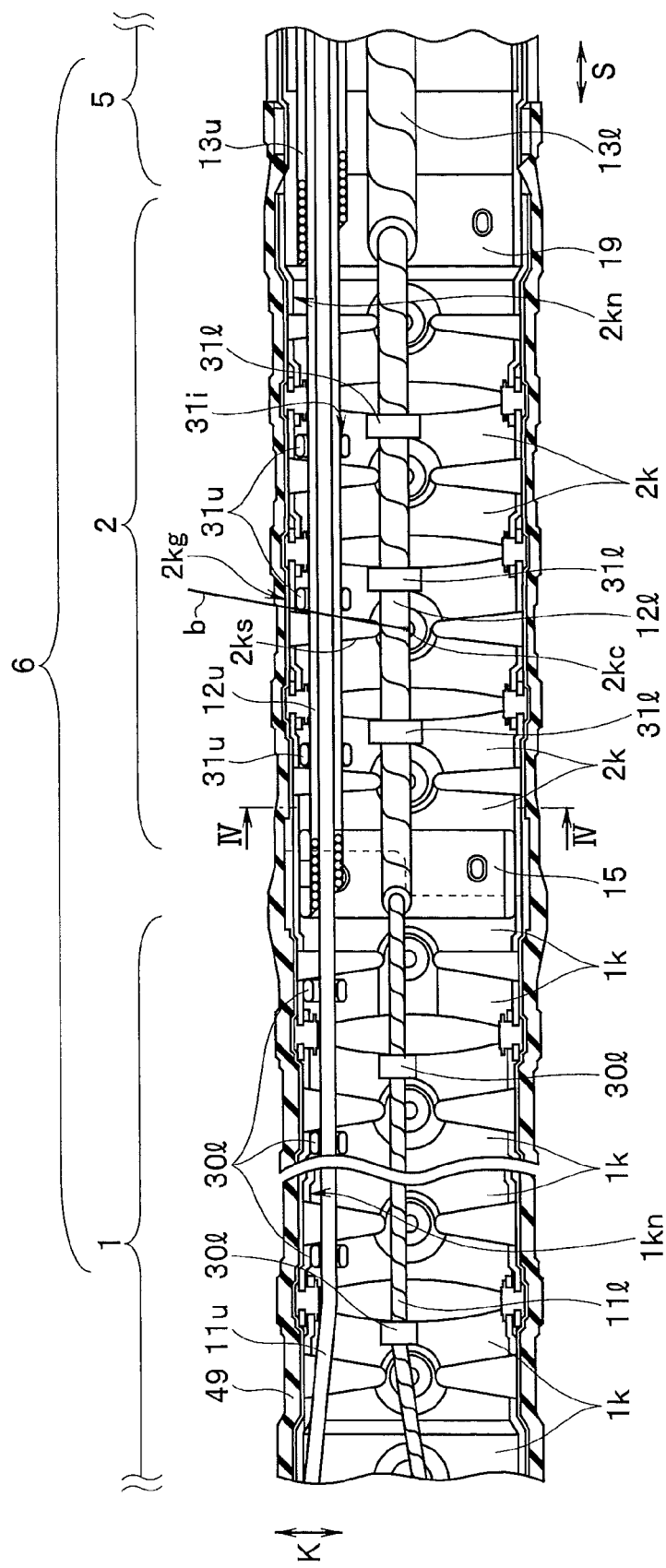
FIG. 2 is a cross-sectional view along a line II-II in FIG. 1 of a distal end side of an insertion portion.
Figure 3:
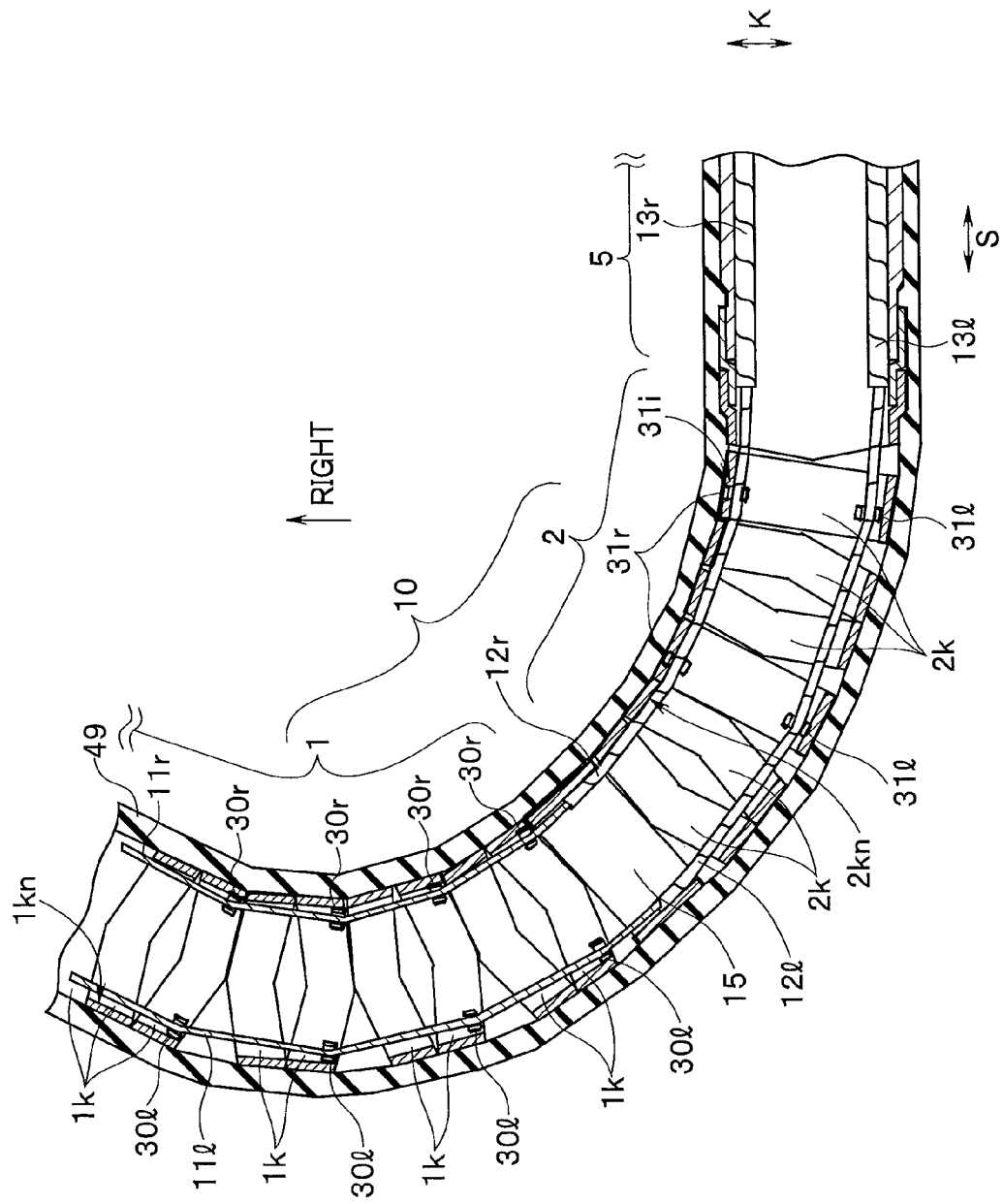
FIG. 3 is a cross-sectional view illustrating a first bending portion and a second bending portion in FIG. 1 being bent toward the RIGHT side in a cutting direction by 90° different in a circumferential direction of the insertion portion in FIG. 2.

FIG. 2 is a cross-sectional view of the distal end side of the insertion portion along a line II-II in FIG. 1 and FIG. 3 is a cross-sectional view illustrating the first bending portion and the second bending portion in FIG. 1 being bent toward the RIGHT side in a cutting direction by 90° different in a circumferential direction of the insertion portion in FIG. 2.

Figure 4:
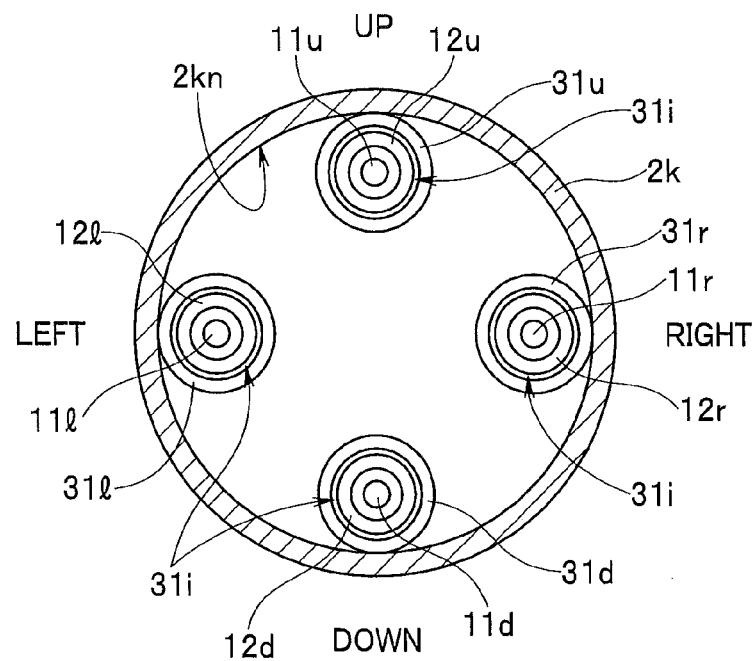
FIG. 4 is a cross-sectional view along a line IV-IV in FIG. 2 of the second bending portion.
Figure 5:
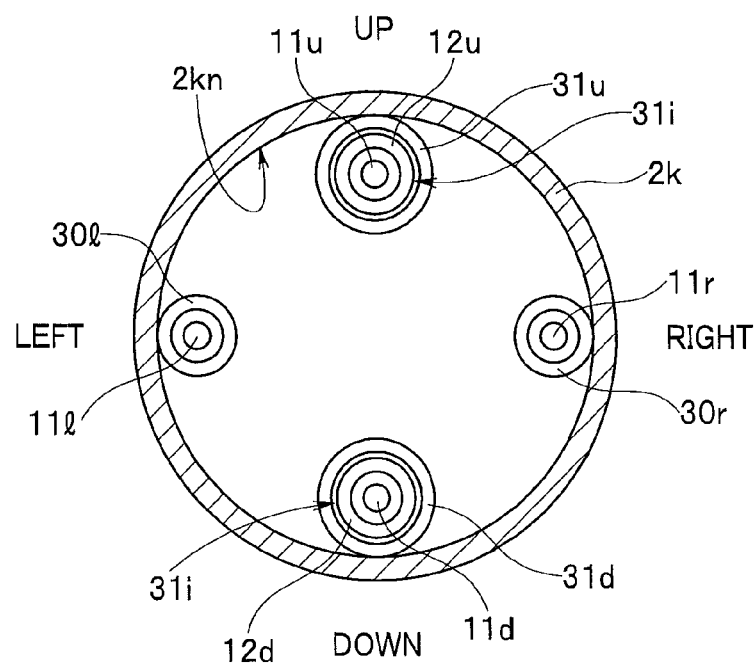
FIG. 5 is a cross-sectional view illustrating a modification in which only a perimeter of each bending operation wire located in an UP direction and DOWN direction in FIG. 4 is covered with a first coil sheath.

FIG. 4 is a cross-sectional view along a line IV-IV in FIG. 2 of the second bending portion and FIG. 5 is a cross-sectional view illustrating a modification in which only a perimeter of each bending operation wire located in an UP direction and DOWN direction in FIG. 4 is covered with a first coil sheath.

As shown in FIG. 2, a plurality of cylindrical first bending pieces 1$k$ are provided inside the first bending portion 1, connected along the longitudinal direction S. Note that the plurality of first bending pieces 1$k$ are pivotably connected so that neighboring bending pieces are connected to each other so as to be bendable in four directions: up, down, left and right, in the longitudinal direction S.

A plurality of cylindrical second bending pieces 2$k$ are also provided inside the second bending portion 2 connected together along the longitudinal direction S. Note that the plurality of second bending pieces 2$k$ are also pivotably connected so that neighboring bending pieces are connected to each other so as to be bendable in four directions: up, down, left and right, in the longitudinal direction S.

Note that, though not shown, blades cover the perimeters of the first bending pieces 1$k$ and the second bending pieces 2$k$ and bending rubber 49 covers the perimeters of the blades.

As shown in FIG. 2 and FIG. 3, the first bending portion 1 and the second bending portion 2 are connected together along the longitudinal direction S via a connection pipe sleeve 15.

More specifically, the first bending piece 1$k$ located closest to the proximal end side in the first bending portion 1 and the second bending piece 2$k$ located closest to the distal end side in the second bending portion 2 are fitted to the perimeter of the connection pipe sleeve 15, and the first bending portion 1 and the second bending portion 2 are thereby connected together via the connection pipe sleeve 15.

Note that instead of using the connection pipe sleeve 15 to connect the first bending portion 1 and the second bending portion 2, the proximal end of the first bending portion 1 may be directly connected to the distal end of the second bending portion 2.

Inside the insertion portion 6 and the operation section 7, for example, four bending operation wires (hereinafter, simply referred to as "wires") 11$r$, 11$l$, 11$u$ and 11$d$ which are freely movable forward and backward (hereinafter, simply referred to as "front-back") in the longitudinal direction S to cause the first bending portion 1 or the first bending portion 1 and the second bending portion 2 to bend are inserted shifted by approximately 90° from each other in the circumferential direction of the insertion portion 6 as shown in FIG. 4.

A distal end of each wire 11$r$ to 11$d$ is fixed to the first bending piece 1$k$ located closest to the distal end side among the plurality of first bending pieces 1$k$.

As shown in FIG. 2 and FIG. 3, a plurality of tubular guides 30 that hold the wires 11$r$ to 11$d$ so that the wires 11$r$ to 11$d$ run along an inner surface 1$kn$ of each first bending piece 1$k$ and located shifted by approximately 90° from each other in the circumferential direction are fixed to the inner surface 1$kn$ of each first bending piece 1$k$. Note that in FIG. 2, the wire 11$d$ is omitted for simplicity of illustration.

Note that each proximal end of the two up-down bending wires 11$u$ and 11$d$ is wound around the aforementioned up-down bending pulley and each proximal end of the two right-left bending wires 11$r$ and 11$l$ is wound around the aforementioned right-left bending pulley.

That is, when the bending operation knob 41 is operated, one of the two up-down wires 11$u$ and 11$d$ is moved backward and the other is moved forward by the up-down bending pulley. That is, the one is pulled and the other is loosened. This causes the first bending portion 1 or the first bending portion 1 and the second bending portion 2 to bend in any one of the UP direction and the DOWN direction.

In addition, when the bending operation knob 42 is operated, one of the two right-left wires 11$r$ and 11$l$ is moved backward and the other is moved forward by the right-left bending pulley, that is, the one is pulled and the other is loosened. This causes the first bending portion 1 or the first bending portion 1 and the second bending portion 2 to bend in any one of the RIGHT direction and the LEFT direction.

A distal end side of a connection member 19 is fixed to the second bending piece 2$k$ located closest to the proximal end side in the second bending portion 2 among the plurality of second bending pieces 2k. Furthermore, a distal end side of the blade making up the flexible tubular part 5 is fixed to the perimeter of the proximal end side of the connection member 19. Note that the perimeter of the blade is covered with a sheathing tube.

Furthermore, the perimeters of the four wires 11r to 11d inserted into the operation section 7 and the insertion portion 6 are covered with inside coil sheaths 12r, 12l, 12u and 12d respectively, which are the first coil sheaths made up, for example, of flexible and elongated coil pipes along the longitudinal direction S as shown in FIG. 4. Note that in FIG. 2, the inside coil sheath 12d is omitted for simplicity of illustration.

That is, in the operation section 7 and the insertion portion 6, the four inside coil sheaths 12r to 12d are inserted at positions shifted by approximately 90° from each other in the circumferential direction of the insertion portion 6. Note that each of the inside coil sheaths 12r to 12d is formed of a stainless steel coil pipe, for example.

Note that each inside coil sheath 12r to 12d is made up of the flexible coil pipe because if the perimeter of each wire 11r to 11d is covered with a normal metallic rigid pipe, not only the bending portion 10 would not bend but also the flexibility of the flexible tubular part 5 would deteriorate.

The material that makes up each inside coil sheath 12r to 12d is not limited to the coil as long as each inside coil sheath 12r to 12d does not cause the bendability of the bending portion 10 or the flexibility of the flexible tubular part 5 to deteriorate and can resist a compressive force acting along the longitudinal direction S of each coil sheath 12r to 12d when the bending portion 10 is bent.

Furthermore, as shown in FIG. 5, the inside coil sheaths may also be used to cover only the perimeter of the wire 11u located in the UP direction and the perimeter of the wire 11d located in the DOWN direction as the inside coil sheaths 12u and 12d. That is, the perimeters of the wires 11r and 11l may not be covered with the inside coil sheaths.

On the contrary, only the perimeters of the wires 11r and 11l are covered with the inside coil sheaths 12r and 12l, and the perimeters of the wires 11u and 11d may not be covered with the inside coil sheaths.

Furthermore, in each inside coil sheath 12r to 12d, each wire 11r to 11d is freely movable forward or backward.

Furthermore, as shown in FIG. 2 and FIG. 3, the distal end of each inside coil sheath 12r to 12d is fixed to the distal end of the second bending portion 2, or more specifically, to the connection pipe sleeve 15, for example, by brazing.

Note that for each proximal end of each inside coil sheath 12r to 12d, it is possible to switch between a fixed state and an unfixed state through the aforementioned switching mechanism provided for the operation section 7.

Furthermore, as shown in FIG. 2 and FIG. 3, the perimeters of the four inside coil sheaths 12r to 12d located in the flexible tubular part 5 are covered with outside coil sheaths 13r, 13l, 13u and 13d (outside coil sheath 13d is not shown) which are second coil sheaths made up, for example, of flexible coil pipes.

Note that each inside coil sheath 12r to 12d inserted in each outside coil sheath 13r to 13d is freely movable forward or backward in the longitudinal direction S. Moreover, each inside coil sheath 12r to 12d is also formed, for example, of a stainless steel coil pipe.

Note that if each wire 11r to 11d is double covered with coil sheaths used for conventional products, the flexibility of the flexible tubular part 5 deteriorates. Accordingly, in the present embodiment, the thickness and material of the coil sheath and the cross-sectional shape of a coil elemental wire 12s (see FIG. 7) are devised so that the coil sheath withstands pulling forces of the wires 11r to 11d as well as the inside and outside coil sheaths, is not buckled by a compressive force acting so as to bend the bending portion 10 and the double sheath does not cause the flexibility of the flexible tubular part 5 to considerably deteriorate, and the coil sheath is formed of a flexible material.

Thus, the material of each outside coil sheath 13r to 13d is not limited to a coil as long as it does not cause the flexibility of the flexible tubular part 5 to deteriorate and can resist a compressive force acting in the longitudinal direction S of each outside coil sheath 13r to 13d when the bending portion 10 is bent.

As shown in FIG. 2 and FIG. 3, the distal end of each outside coil sheath 13r to 13d is fixed to the distal end of the flexible tubular part 5, or more specifically, to the connection member 19 by, for example, brazing. Furthermore, the proximal end of each outside coil sheath 13r to 13d is fixed to a stopper member, which is not shown, by, for example, brazing inside the proximal end of the flexible tubular part 5 or inside the operation section 7.

Thus, since each outside coil sheath 13r to 13d is inserted with the distal end and the proximal end fixed inside the flexible tubular part 5, when one of the four wires 11r to 11d is pulled to bend the bending portion 10, each outside coil sheath 13r to 13d resists a compressive force acting on the flexible tubular part 5 along the longitudinal direction S of each outside coil sheath 13r to 13d. This prevents even the flexible tubular part 5 from being bent together with the bending portion 10.

Note that in a state in which the distal end and the proximal end of each outside coil sheath 13r to 13d are fixed, the distal end of each inside coil sheath 12r to 12d is fixed to the connection pipe sleeve 15 and the proximal end is formed to a length in the longitudinal direction S so that the proximal end is not drawn toward the distal end side rather than the proximal end of each outside coil sheath 13r to 13d.

Thus, in such a configuration, when wishing to bend the first bending portion 1 and the second bending portion 2 first, the operator cancels the fixing of the proximal end of each inside coil sheath 12r to 12d by the aforementioned switching member without operating the switching lever 43.

In this condition, the operator operates either the bending operation knob 41 or 42 to pull any one of the four wires 11r to 11d, for example, the wire 11r. As a result, since the proximal end of each inside coil sheath 12r, 12u, 12d is not fixed, each inside coil sheath 12r, 12u, 12d cannot resist a compressive force acting along the longitudinal direction S of each inside coil sheath 12r, 12u, 12d in the second bending portion 2 and each proximal end moves rearward.

Since the distal end and the proximal end of each outside coil sheath 13r to 13d are fixed in the flexible tubular part 5, each outside coil sheath 13r to 13d resists a compressive force acting along the longitudinal direction S of each outside coil sheath 13r to 13d.

As a result, as shown in FIG. 3, the first bending portion 1 and the second bending portion 2 are bent toward the RIGHT direction. Note that the same applies to a case where the first bending portion 1 and the second bending portion 2 are bent toward any one of the LEFT direction, UP direction, and DOWN direction.

Next, when wishing to bend only the first bending portion 1, the operator operates the switching lever 43 to cause the switching member to fix the proximal end of each inside coil sheath 12r to 12d.

In this condition, the operator operates either the bending operation knob 41 or 42 to pull any one of the four wires 11r to 11d, for example, the wire 11r. Then, since the proximal end of each inside coil sheath 12r to 12d is fixed, the second bending portion 2 resists the compressive force acting along the longitudinal direction S of each inside coil sheath 12r to 12d. As a result, only the first bending portion 1 is bent toward the RIGHT direction. Note that the same applies to a case where only the first bending portion 1 is bent toward any one of the LEFT direction, the UP direction and the DOWN direction.

Here, as shown in FIG. 5, when the perimeters of the wires 11r and 11l are not covered with the inside coil pipe, the first bending portion 1 and the second bending portion 2 are bent toward the RIGHT direction or LEFT direction through operation of the bending operation knob 42.

However, those bendable toward only the UP direction or DOWN direction are used for the plurality of second bending pieces 2k making up the second bending portion 2, that is, when the neighboring bending pieces are pivotably connected so as to be bent toward only the UP direction or DOWN direction, it is possible to bend only the first bending portion 1 toward the RIGHT direction or LEFT direction through operation of the bending operation knob 42.

The same applies to a case where only the perimeters of the wires 11u and 11d are not covered with the inside coil pipe, and in this case, the first bending portion 1 and the second bending portion 2 are bent toward the UP direction or DOWN direction through operation of the bending operation knob 41.

However, when those only bendable toward the RIGHT direction or LEFT direction are used for the plurality of second bending pieces 2k making up the second bending portion 2, that is, when neighboring bending pieces are pivotably connected so as to be bent only toward the RIGHT direction or LEFT direction, it is possible to bend only the first bending portion 1 toward the UP direction or DOWN direction through operation of the bending operation knob 41.

From above, in the configuration shown in FIG. 5, it is not possible to switch between bending of the first bending portion 1 and the second bending portion 2 toward the RIGHT direction or LEFT direction and bending of only the first bending portion 1, whereas it is possible to bend only the first bending portion 1 toward the RIGHT direction or LEFT direction.

Here, as shown in FIG. 2 to FIG. 4, a plurality of guides 31r, 31l, 31u and 31d which are guide sections are fixed to an inner surface 2kn of each of the plurality of second bending pieces 2k by, for example, brazing in the second bending portion 2.

The guides 31r, 31l, 31u and 31d are made up of tubular members that include through holes 31i which the inside coil sheaths 12r to 12d penetrate in the longitudinal direction S and hold each inside coil sheath 12r to 12d so that the inside coil sheaths 12r to 12d penetrating the through holes 31i run along the inner surface 2kn of each second bending piece 2k and are arranged shifted by approximately 90° from each other in the circumferential direction.

Note that, as shown in FIG. 2, the guides 31r to 31d are fixed at a position at which the guides 31r to 31d are not protruding ahead of a line b connecting a rotating shaft 2kc where neighboring bending pieces in the longitudinal direction S provided at a distal end 2ks of each second bending piece 2k and a distal end of an outer circumferential face 2kg of the second bending pieces 2k, that is, the distal end of a shoulder of the second bending pieces 2k with respect to the inner surface 2kn of the second bending pieces 2k, in other words, a position where the guides 31r to 31d overlap with the second bending pieces 2k.

When even part of the guides 31r to 31d is fixed so as to protrude ahead of the line b, the guides 31r to 31d come very close to the forward neighboring second bending piece 2k. For this reason, when the second bending portion 2 is bent depending on the bending direction, the guides 31r to 31d comes into contact with the forward neighboring second bending pieces 2k, interfering with the bending of the second bending portion 2.

Thus, since the plurality of guides 31r to 31d are fixed to the inner surface 2kn of the plurality of second bending pieces 2k, it is possible to prevent the inside coil sheaths 12r to 12d from moving other than the longitudinal direction S as the second bending portion 2 is bent as described above. That is, the guides 31r to 31d allow the inside coil sheaths 12r to 12d to be held movable forward or backward always at a fixed position with respect to the second bending pieces 2k.

Note that as shown in FIG. 5, when the perimeters of the wires 11r and 11l are not covered with the inside coil sheaths 12r and 12l, on the inner surface 2kn of each of the plurality of second bending pieces 2k, the plurality of guides 30r and 30l that hold the wires 11r and 11l may be fixed at positions shifted by 90° from the guides 31u and 31d in the circumferential direction so that the wires 11r and 11l run along the inner surface 2kn of each of the plurality of second bending pieces 2k.

Figure 6:
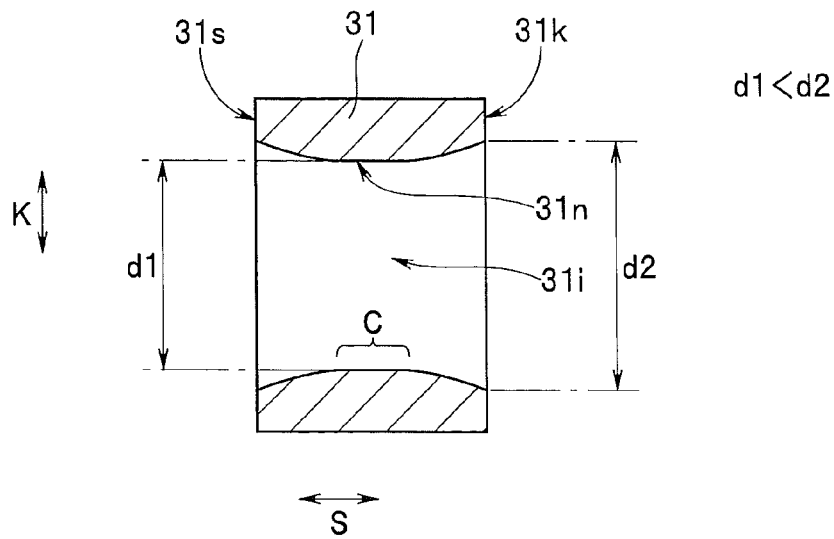
FIG. 6 is an enlarged cross-sectional view illustrating a guide provided in the second bending piece in FIG. 2.

Next, the shapes of the guides 31r to 31d will be described using FIG. 6. FIG. 6 is an enlarged cross-sectional view of the guide provided in the second bending piece in FIG. 2. Note that, since the guide 31r to guide 31d have the same shape, they are represented by a guide 31 in FIG. 6.

As shown in FIG. 6, an inner surface 31n formed by the through hole 31i in the guide 31 has a central part C in the longitudinal direction S which protrudes inside in a diameter direction K more than a distal end 31s side and a proximal end 31k side of the guide 31 (d1<d2).

More specifically, the inner surface 31n is formed into such a shape that the diameter of the through hole 31i smoothly decreases from the distal end 31s and the proximal end 31k to the central part C.

That is, the guide 31 of the present embodiment is formed into such a shape that a corner part between the inner surface 31n and the distal end 31s and a corner part between the inner surface 31n and the proximal end 31k are removed from the inner surface 31n.

Figure 7:
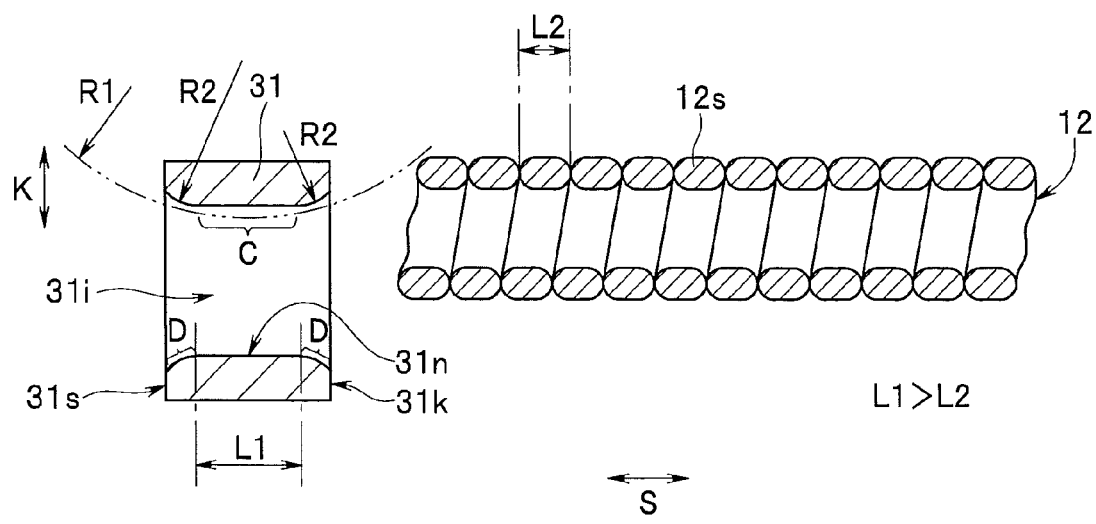
FIG. 7 is a cross-sectional view illustrating a modification of the shape of the inner surface of the guide in FIG. 6 together with the inside coil sheath.

Thus, the inside coil sheaths 12r to 12d are configured by winding a coil elemental wire 12s as shown in FIG. 7, which will be described later, to thereby have such flexibility that it is bendable together with the second bending portion 2 as described above. As the second bending portion 2 is bent, when any one of the inside coil sheaths 12r to 12d slides forward or backward through the through hole 31i of each guide 31 that holds each inside coil sheath 12r to 12d, this prevents any one of the inside coil sheaths 12r to 12d from being caught in the corner part between the inner surface 31n and the distal end 31s or the proximal end 31k.

Figure 20:
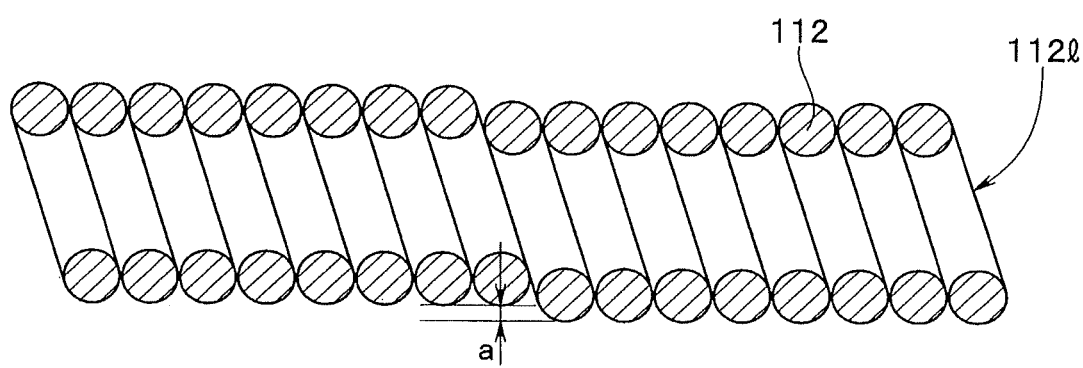
FIG. 20 is an enlarged cross-sectional view illustrating the left inside coil pipe in FIG. 14.

This prevents the phenomenon as shown in aforementioned FIG. 20 that the coil elemental wire is disarrayed, that is, a pitch shift occurs, sliding properties of the inside coil sheaths 12r to 12d with respect to the through hole 31i deteriorate, consequently causing the bending shape of the second bending portion 2 to vary every time bending takes place.

Note that friction-reducing treatment for reducing friction with the inside coil sheaths 12r to 12d may be applied to the inner surface 31n in order to improve sliding properties of the inside coil sheaths 12r to 12d with respect to the inner surface 31n. An example of friction-reducing treatment is a technique of applying a coating agent containing molybdenum disulfide to the inner surface 31n.

Figure 8:
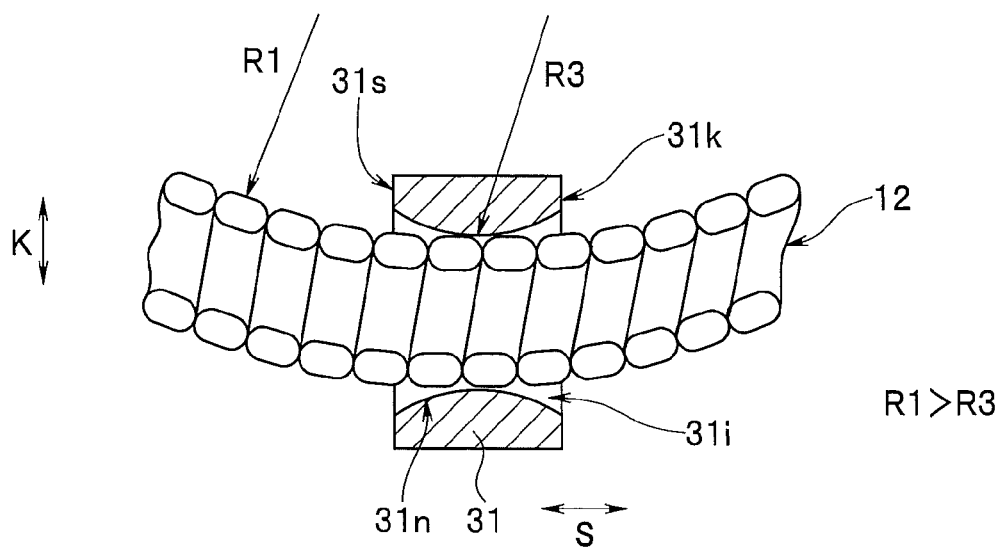
FIG. 8 is a cross-sectional view illustrating a modification of the shape of the inner surface of the guide in FIG. 6 different from FIG. 7 in a state in which an inside coil sheath is inserted into a through hole.
Figure 9:
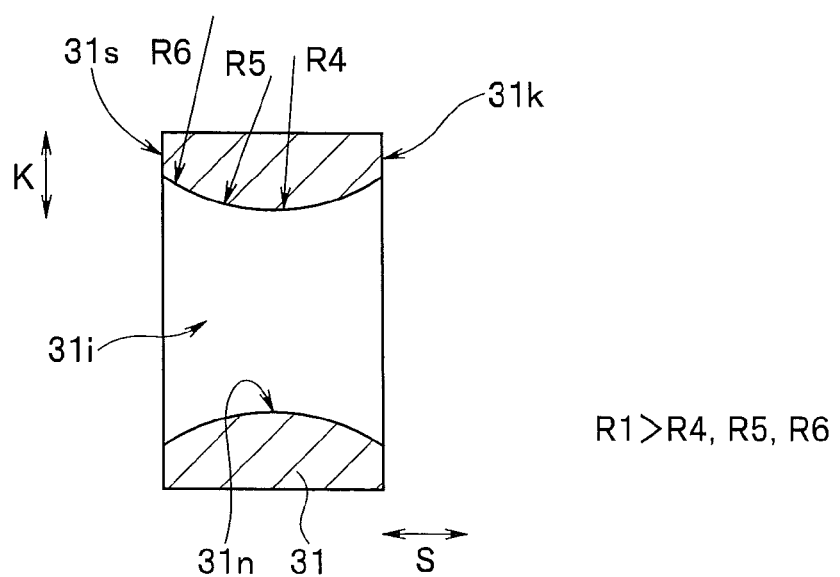
FIG. 9 is a cross-sectional view illustrating a modification of the shape of the inner surface of the guide in FIG. 8.

Examples of the aforementioned shape of the inner surface 31n with the corner parts removed by adopting the shape with the central part C of the inner surface 31n protruding inside in the diameter direction K more than the distal end 31s side and the proximal end 31k side (d1<d2) include shapes shown in FIG. 7 to FIG. 9.

FIG. 7 is a cross-sectional view illustrating a modification of the shape of an inner surface of the guide in FIG. 6 together with the inside coil sheath, FIG. 8 is a cross-sectional view illustrating a modification of the shape of the inner surface of the guide in FIG. 6 different from FIG. 7 in a state in which an inside coil sheath is inserted into the through hole and FIG. 9 is a cross-sectional view illustrating a modification of the shape of the inner surface of the guide in FIG. 8.

Note that in FIG. 7 to FIG. 9, since the guide 31r to guide 31d have the same shape, these guides are represented by the guide 31 and since the inside coil sheaths 12r to 12d also have the same shape, they are represented by the inside coil sheath 12.

As shown in FIG. 7, the inner surface 31n may be formed into a shape in which the central part C has a predetermined length L1 along the longitudinal direction S and the hole diameter of the through hole 31i at the central part C is constant along the longitudinal direction S as long as the central part C protrudes (d1<d2) inside in the diameter direction K more than the distal end 31s side and the proximal end 31k side.

In this case, the length L1 of the central part C needs to be formed to be longer than a length L2 in the longitudinal direction S of the coil elemental wire 12s making up the inside coil sheath 12 (L1>L2). Moreover, the length L1 is preferably formed to be greater than twice the length L2 (L1>2L2).

This is because if the length L2 is greater than the length L1, stress may be concentrated on the one coil elemental wire 12s that comes into contact with the inner surface 31n making it more likely that the aforementioned pitch shifts will occur and the inside coil sheath 12 that slides over the inner surface 31n will be caught in the inner surface 31n.

As shown in FIG. 7, a region D of the inner surface 31n connecting the distal end 31s or proximal end 31k and the central part C is formed into a curved surface. The radius of curvature R2 of the curved surface is set to be smaller than a bending radius R1 of the inside coil sheath 12 that passes through the through hole 31i when the second bending portion 2 is bent at a maximum bending angle (R2<R1).

This not only eliminates the corner parts in the vicinity of the distal end 31s and the proximal end 31k of the inner surface 31n but also allows the region D to be formed into a smooth curved surface, and thereby prevents the inside coil sheath 12 from being caught in the inner surface 31n even when the inside coil sheath 12 slides through the through hole 31i with the second bending portion 2 being bent at a maximum bending angle.

Furthermore, as shown in FIG. 8, the whole inner surface 31n may be formed into a curved surface as long as it has a shape in which the central part C protrudes inside in the diameter direction K more than the distal end 31s side and the proximal end 31k side (d1<d2).

In this case, a radius of curvature R3 of the inner surface 31n is set to be smaller than the bending radius R1 of the inside coil sheath 12 that passes through the through hole 31i (R3<R1) when the second bending portion 2 is bent at a maximum bending angle.

Note that the inner surface 31n may be formed into a curved surface, a radius of curvature of which varies such as R4, R5 and R6 as shown in FIG. 9 instead of the constant radius of curvature. In this case, the radius of curvatures R4, R5 and R6 need to be set to be smaller than the bending radius R1 as well (R4, R5, R6<R1).

This not only eliminates the corner parts in the vicinity of the distal end 31s and the proximal end 31k of the inner surface 31n but also causes the inner surface 31n to be formed into a smooth curved surface, and thereby prevents the inside coil sheath 12 from being caught in the inner surface 31n even when the inside coil sheath 12 slides through the through hole 31i with the second bending portion 2 being bent at a maximum bending angle.

The present embodiment has shown that the plurality of guides 31r, 31l, 31u and 31d for holding the respective inside coil sheaths 12r to 12d so as to run along the inner surfaces 2kn of the respective second bending pieces 2k are fixed to the inner surfaces 2kn of the plurality of second bending pieces 2k.

The present embodiment also has shown that the inner surfaces 31n of the guides 31r to 31d are formed so that the central part C protrudes inside in the diameter direction K more than the distal end 31s side and the proximal end 31k side (d1<d2).

Accordingly, the guides 31r to 31d cause the inside coil sheaths 12r to 12d to be always kept at constant positions with respect to the second bending pieces 2k, that is, the guides 31r to 31d prevent the inside coil sheaths 12r to 12d from moving in other than the longitudinal direction S in the second bending pieces 2k as the second bending portion 2 is bent, and can thereby keep the bending shape constant for each bending operation of the second bending portion 2.

Furthermore, it is possible to prevent the inside coil sheaths 12r to 12d that slide forward or backward from being caught in the inner surfaces 31n of the guides 31r to 31d as the second bending portion 2 is bent. This prevents the bending shape of the second bending portion 102 from varying for each bending operation caused by pitch shifts generated in the inside coil sheaths 12r to 12d when the inside coil sheaths 12r to 12d are caught in the inner surface 31n, thus deteriorating sliding properties of the inside coil sheaths 12r to 12d in the through hole 31i. That is, it is possible to keep the bending shape constant for each bending operation of the second bending portion 2.

Figure 17:
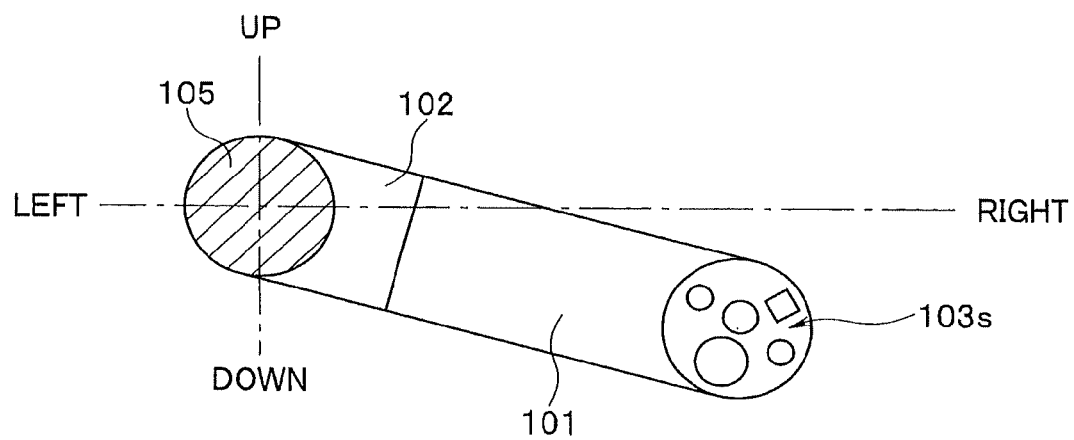
FIG. 17 is a partial cross-sectional view along a line XVII-XVII in FIG. 13 illustrating an example in which the second bending portion is bent by being shifted from the RIGHT side toward the DOWN side.
Figure 18:
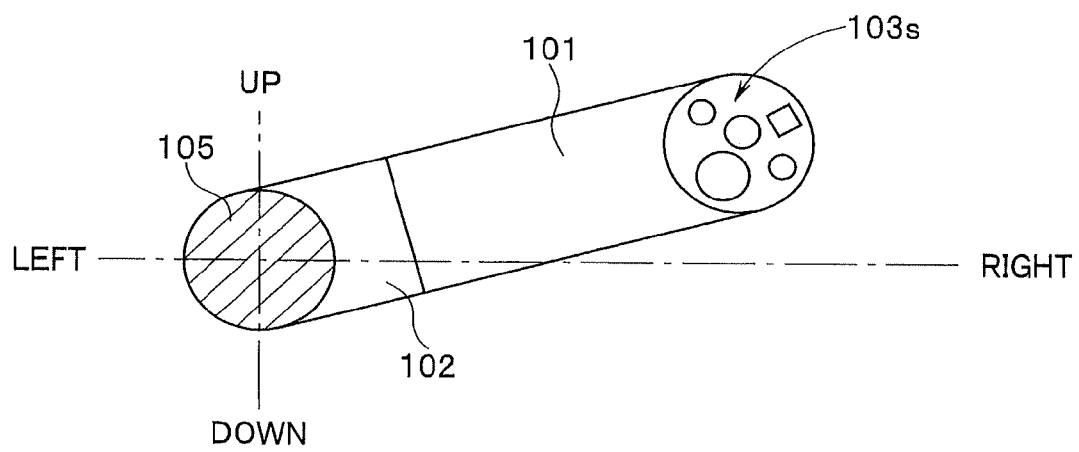
FIG. 18 is a partial cross-sectional view illustrating an example in which the second bending portion in FIG. 13 is bent by being shifted from the RIGHT side toward the UP side.
Figure 19:
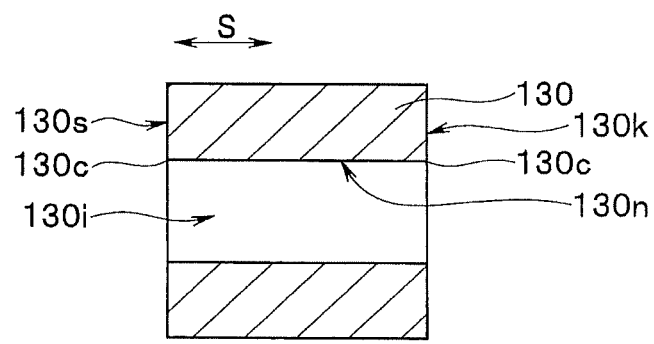
FIG. 19 is an enlarged cross-sectional view of a wire guide section provided in the first bending piece in FIG. 14.

More specifically, when the second bending portion 2 is bent toward the RIGHT direction, it is possible to prevent the bending direction of the second bending portion from being shifted from the RIGHT side to the DOWN side as shown in aforementioned FIG. 17. Moreover, as shown in FIG. 18, it is possible to prevent the bending direction of the second bending portion from being shifted from the RIGHT side to the UP side. Thus, it is possible to reliably bend the second bending portion 2 toward the RIGHT direction for each bending operation. Note that the same applies to a case where the second bending portion 2 is bent toward the LEFT direction, UP direction or DOWN direction.

As described so far, it is possible to provide the endoscope 50 having a configuration capable of keeping the bending shape of the second bending portion 2 constant for each bending operation.

Note that it goes without saying that the shape of the inner surface 31n of the aforementioned guide 31 may be applicable to the shape of the inner surface of the guide 30 that holds the wires 11r to 11d.

Figure 10:
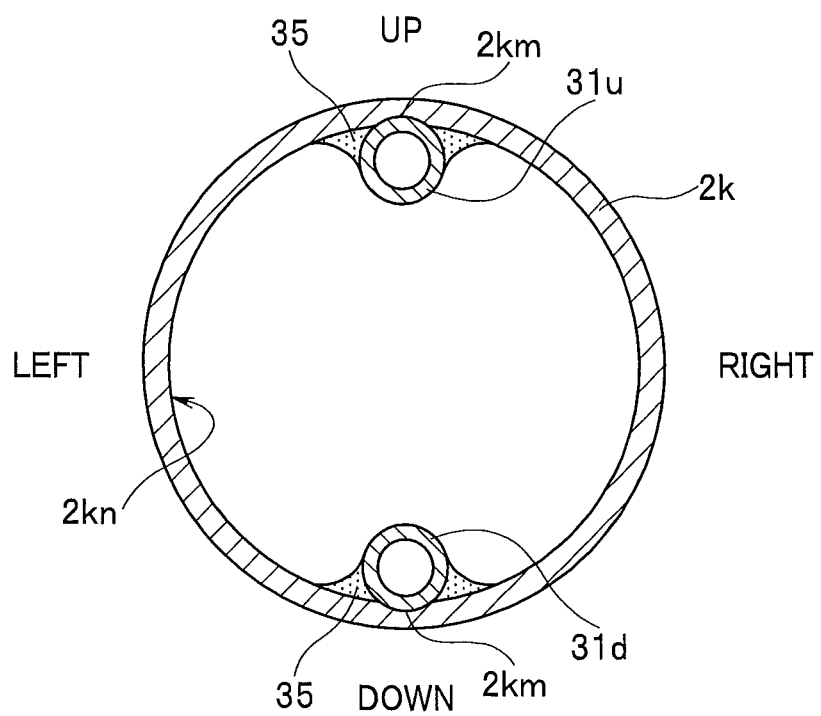
FIG. 10 is a cross-sectional view illustrating a modification in which a groove into which part of the guide is fitted is provided in the inner surface of the second bending piece in FIG. 4.

Note that hereinafter, a modification will be described using FIG. 10. FIG. 10 is a cross-sectional view illustrating a modification in which a groove into which part of the guide is fitted is provided in the inner surface of the second bending piece in FIG. 4. Note that in FIG. 10, the inside coil sheaths on the RIGHT direction and the LEFT direction side, and further the wires 11r to 11d are omitted.

As shown in FIG. 10, when the guides 31u and 31d are fixed to the inner surface 2kn of the second bending piece 2k, grooves 2km into which parts of the guides 31u and 31d are fitted may be formed at fixed positions.

In such a configuration, the guides 31u and 31d are fixed to the inner surface 2kn by brazing 35 or the like with parts of the guides 31u and 31d being fitted into the grooves 2km.

Note that, though not shown, the grooves 2km into which parts of the guides 31r and 31l are fitted may also be formed at fixed positions of the guides 31r and 31l on the inner surface 2kn.

According to such a configuration, when the guides 31r and 31l are made up of tubular members, it is possible to secure a larger space in the second bending piece 2k by an amount of space corresponding to parts of the guides 31r and 31l fitted in the grooves 2km. Note that the other effects are the same as those in the aforementioned present embodiment.

Second Embodiment

Figure 11:
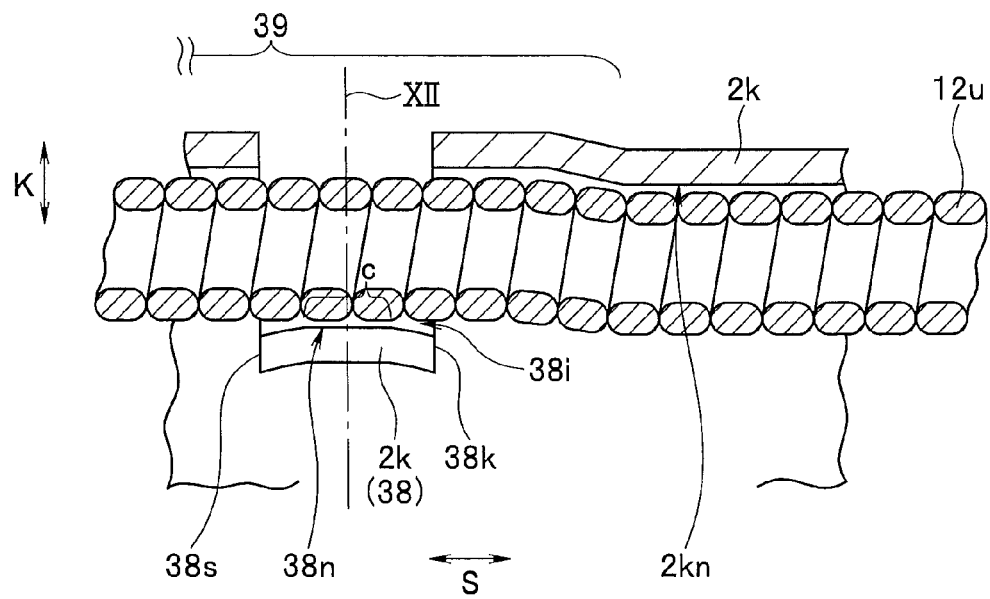
FIG. 11 is a partial cross-sectional view of the second bending portion of an insertion portion of an endoscope illustrating a second embodiment.
Figure 12:
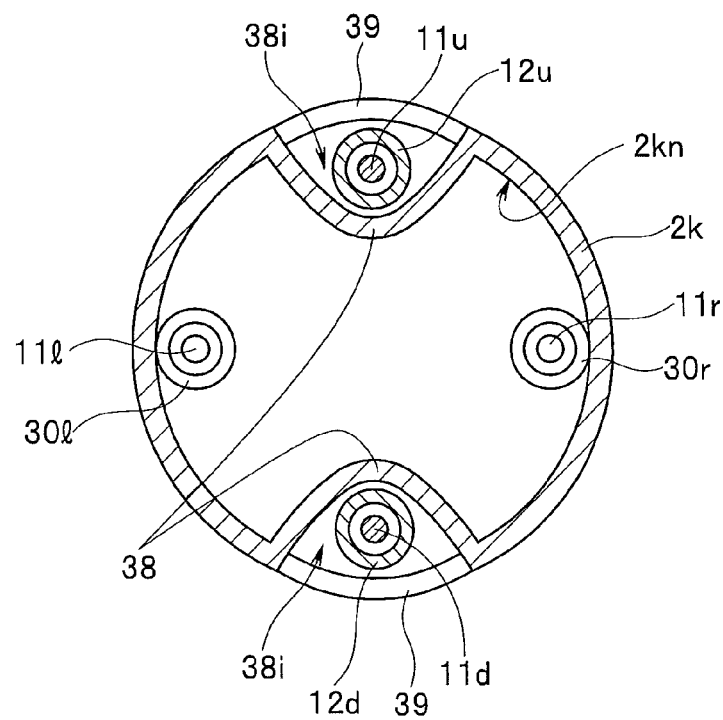
FIG. 12 is a cross-sectional view along a line XII in FIG. 11 of the second bending piece.
Figure 13:
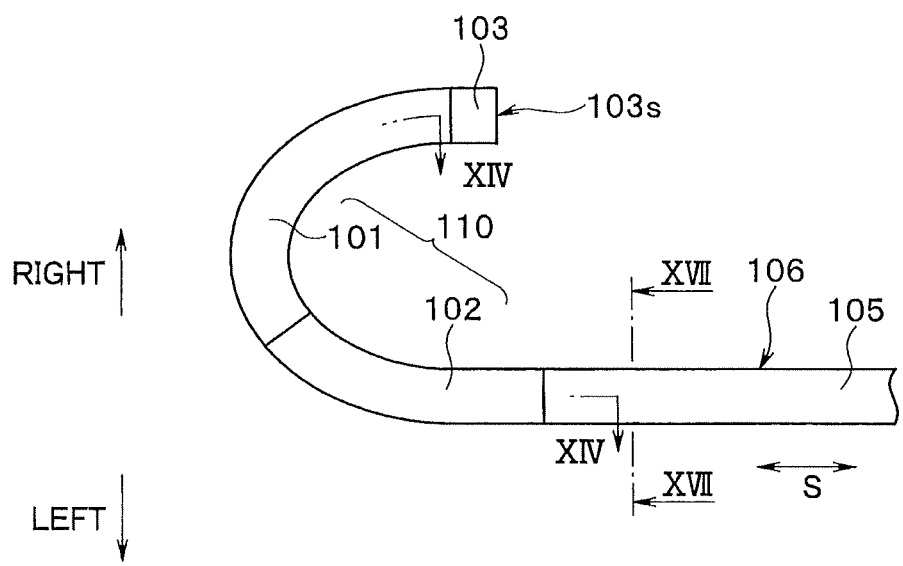
FIG. 13 is a diagram schematically illustrating a state in which the second bending portion together with the first bending portion is bent toward the RIGHT direction on a distal end side of an insertion portion of a conventional endoscope.
Figure 14:
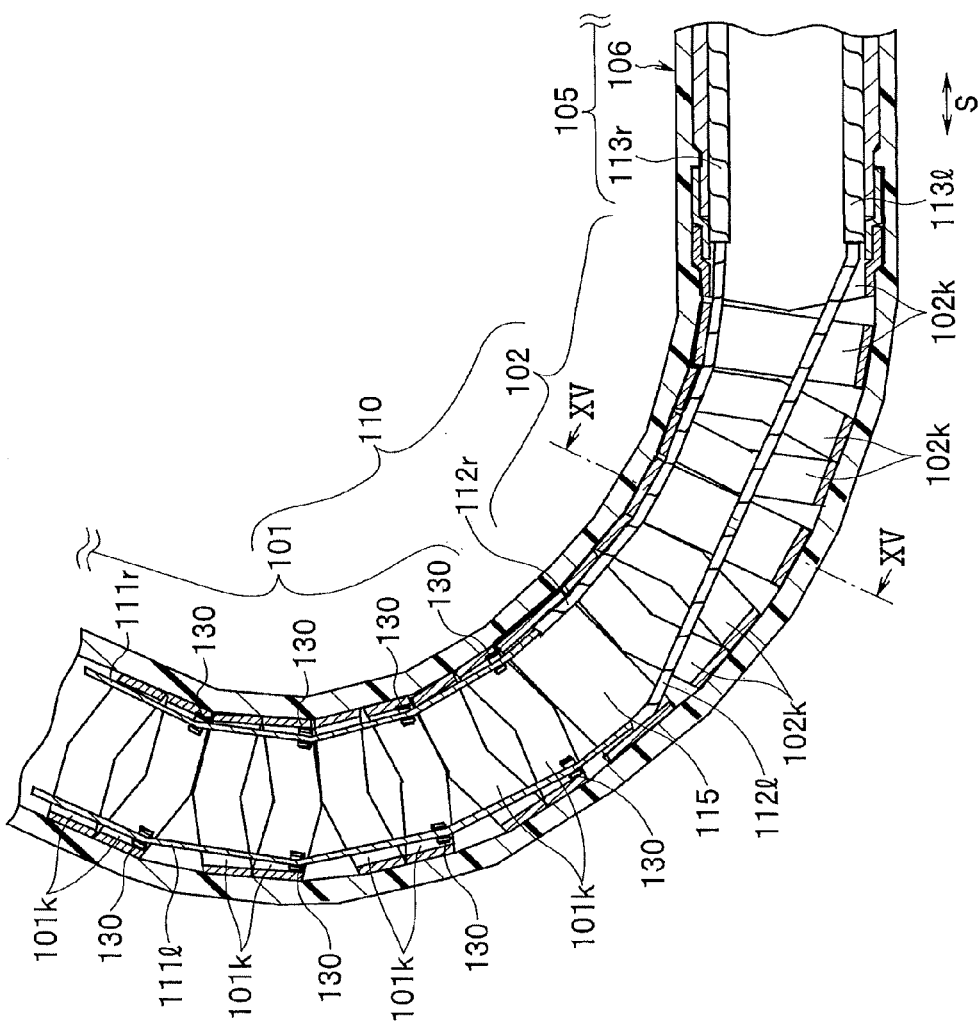
FIG. 14 is a cross-sectional view along a line XIV-XIV in FIG. 13 of the first bending portion and the second bending portion.
Figure 15:
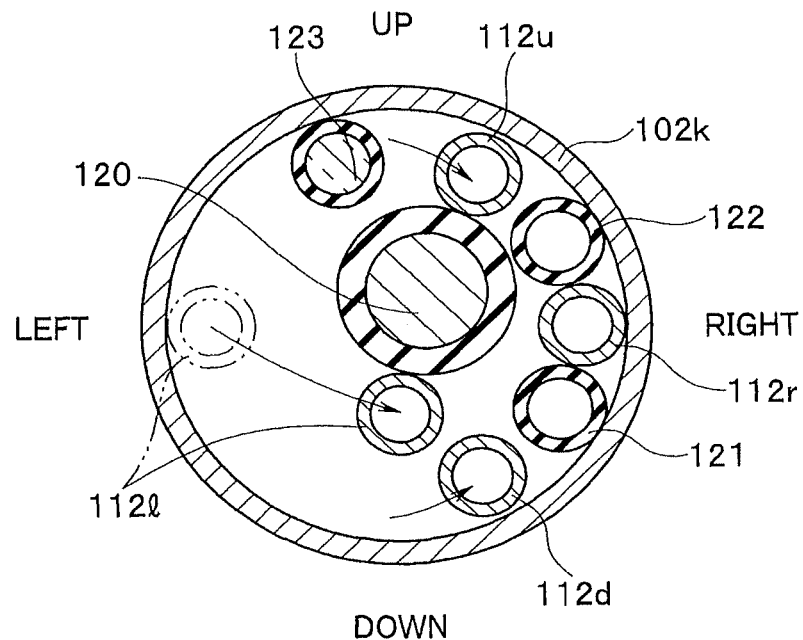
FIG. 15 is a cross-sectional view along a line XV-XV in FIG. 14 illustrating an example in which a left inside coil pipe that moves toward the RIGHT side in FIG. 14 is shifted toward the DOWN side in the second bending piece making up the second bending portion.
Figure 16:
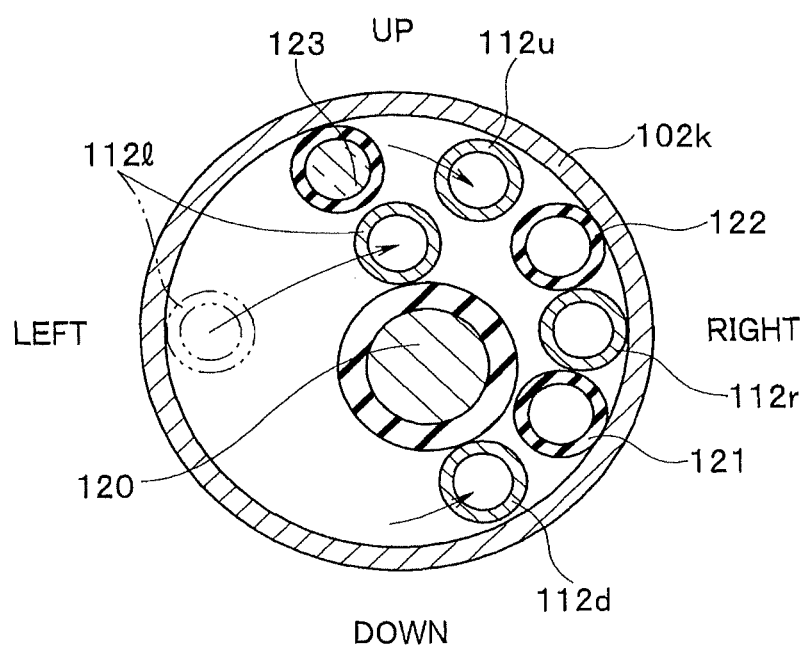
FIG. 16 is a cross-sectional view illustrating an example in which the left inside coil pipe moving toward the RIGHT side in FIG. 14 is shifted toward the UP side.

FIG. 11 is a partial cross-sectional view of a second bending portion of an insertion portion of an endoscope illustrating a second embodiment and FIG. 12 is a cross-sectional view along a line XII in FIG. 11 of the second bending piece.

The configuration of an endoscope of this second embodiment is different from the aforementioned endoscope of the first embodiment shown in FIG. 1 to FIG. 9 in that guides for holding inside coil sheaths are formed integrally with the second bending piece. Thus, only this difference will be described and the same components as those in the first embodiment will be assigned the same reference numerals and description thereof will be omitted.

Note that FIG. 11 shows only the guide that holds the inside coil sheath 12u for simplicity of illustration. Furthermore, FIG. 12 shows, by way of example, a case where the perimeters of the wires 11r and 11l are not covered with the inside coil sheaths 12r and 12l as in the case of FIG. 5 for simplicity of illustration.

Thus, as with FIG. 5, the wires 11r and 11l are held to the inner surface 2kn of the second bending piece 12k by the guide 30.

In the present embodiment, as shown in FIG. 11 and FIG. 12, guides 38 which are guide sections are located at the same positions as the guides 31u and 31d of the aforementioned first embodiment with respect to the inner surfaces 2kn of the plurality of second bending pieces 2k.

More specifically, part of the perimeter of the second bending pieces 2k is folded inside in a concave shape in a diameter direction of the second bending piece 2k, and the guide 38 thereby has the through holes 38i through which the inside coil sheaths 12u and 12d penetrate in the longitudinal direction S, the guide 38 being integrated with the second bending pieces 2k.

Note that in the present embodiment, the inner surface 38n formed of the through hole 38i of the guide 38 is formed into a shape in which a central part C protrudes inside more in the diameter direction K in the guide 38 than the distal end 38s side and the proximal end 38k side. Note that the shape of the inner surface 38n may also be the shape shown in FIG. 7 to FIG. 9.

Furthermore, the inner surface 38n may also be subjected to friction-reducing treatment for reducing friction with the inside coil sheaths 12r to 12d as with the aforementioned first embodiment.

In the present embodiment, in order to prevent the bottom surface of the guide 38, that is, the region folded in the concave shape of the guide 38 from excessively protruding inside in the diameter direction of the second bending piece 2k, a protrusion portion 39 which is convex outside in the diameter direction K is formed in the perimeter of the region in which the guide 38 is formed in the second bending piece 2k.

The formation of the protrusion portion 39 makes it possible to reduce the amount of protrusion of the guide 38 in the second bending piece 2k compared to the case where no protrusion portion 39 is formed. That is, it is possible to secure a greater space inside the second bending piece 2k by an amount of space corresponding to the protrusion portion 39.

Note that, though not shown, the guide 38 may also be provided on the inner surface 2k n so as to hold the inside coil sheaths 12r and 12l that cover the perimeters of the wires 11r and 11l.

Furthermore, the functions of the guide 38 are the same as those of the guide 31 of the aforementioned first embodiment. Note that the rest of the configuration is the same as that of the aforementioned first embodiment.

Thus, the present embodiment has shown that the guide 38 is formed integrally with the second bending piece 2k.

For this reason, it is possible to obtain effects similar to those of the aforementioned first embodiment without separately providing any guide, and ease of assembly of the endoscope 50 is thereby improved. Note that the other effects are the same as those of the aforementioned first embodiment.

Note that in the aforementioned first and second embodiments, it has been shown that the present invention is applicable to the configuration of the second bending portion 2 of the bending portion 10 of the endoscope, but without being limited to this, the present invention is also applicable to other insertion devices such as a treatment instrument, having a bending portion and a second bending portion.

What is claimed is:

1. An endoscope comprising:
   an insertion portion that is inserted into a subject;
   a bendable first bending portion that is provided on a distal end side of the insertion portion;
   a bendable second bending portion that is provided in the insertion portion closer to a proximal end side than the first bending portion;
   a bending operation wire that is inserted into the insertion portion, a distal end of the bending operation wire being fixed to the first bending portion;
   a first coil sheath that is inserted into the second bending portion, the bending operation wire being inserted thereinto so as to be freely movable in a longitudinal direction of the insertion portion and a distal end of the first coil sheath being fixed to a distal end side of the second bending portion;

a switching mechanism that switches between fixing and unfixing of a proximal end of the first coil sheath and moves the proximal end of the first coil sheath in the longitudinal direction inside the insertion portion when the proximal end of the first coil sheath is unfixed;

a guide section that is fixed to an inner surface of the second bending portion, comprising a through hole that the first coil sheath penetrates in the longitudinal direction, and holding the first coil sheath penetrating the through hole so that the first coil sheath runs along the inner surface of the second bending portion;

a first region that is formed into a curved surface on an inner surface on a distal end side of the guide section;

a second region that is formed into a curved surface on an inner surface on a proximal end side of the guide section; and a central part that is formed between the first region and the second region on the inner surface of the guide section, has a shape protruding toward a center of the through hole of the guide section relative to the first region and the second region and is formed to have a length in the longitudinal direction longer than a diameter of a wire making up the first coil sheath.

2. The endoscope according to claim 1, wherein the inner surface of the guide section is formed into a shape in which a diameter of the through hole decreases from the distal end and the proximal end of the guide section in the longitudinal direction toward the central part.

3. The endoscope according to claim 2, wherein the central part of the inner surface has a predetermined length along the longitudinal direction and the diameter of the through hole of the central part is constant along the longitudinal direction, and a region that connects the distal end and the proximal end of the guide section on the inner surface and the central part is formed into a curved surface and a radius of curvature of the curved surface is smaller than a bending radius of the first coil sheath that passes through the through hole when the second bending portion is bent at a maximum bending angle.

4. The endoscope according to claim 2, wherein the inner surface of the guide section is formed into a curved surface, and a radius of curvature of the inner surface is smaller than a bending radius of the first coil sheath that passes through the through hole when the second bending portion is bent at a maximum bending angle.

5. The endoscope according to claim 2, further comprising:

bending pieces provided in the second bending portion and connected together along the longitudinal direction to bend the second bending portion; and a groove provided in an inner surface of the bending piece, part of the guide section being fitted into the groove in a region to which the guide section is fixed.

6. The endoscope according to claim 2, further comprising bending pieces provided in the second bending portion, the bending pieces being connected together along the longitudinal direction to bend the second bending portion, wherein the guide section is fixed on the inner surface of the bending pieces at a position where the guide section does not protrude from a line connecting a rotating shaft provided at a distal end of the bending piece in the longitudinal direction and the distal end of an outer circumferential face of the bending piece, toward the distal end of the insertion portion.

7. The endoscope according to claim 1, further comprising bending pieces provided in the second bending portion, the bending pieces being connected together along the longitudinal direction to bend the second bending portion, wherein part of a perimeter of the bending piece is folded in a concave shape inside in a diameter direction of the bending piece so that the guide section has the through hole and is formed integrally with the bending piece.

8. The endoscope according to claim 1, wherein the inner surface of the guide section is subjected to friction-reducing treatment to reduce friction with the first coil sheath contacting the inner surface.

* * * * *